US009382432B1

(12) United States Patent
McDaniel

(10) Patent No.: US 9,382,432 B1
(45) Date of Patent: Jul. 5, 2016

(54) QUANTUM DOT SECURITY INKS

(71) Applicant: Hunter McDaniel, Los Alamos, NM (US)

(72) Inventor: Hunter McDaniel, Los Alamos, NM (US)

(73) Assignee: UbiQD, LLC, Los Alamos, NM (US)

( * ) Notice: Subject to any disclaimer, the term of this patent is extended or adjusted under 35 U.S.C. 154(b) by 0 days.

(21) Appl. No.: 14/860,676

(22) Filed: Sep. 21, 2015

(51) Int. Cl.
| | |
|---|---|
| C09D 11/03 | (2014.01) |
| C09D 5/22 | (2006.01) |
| G01N 21/64 | (2006.01) |
| C09D 11/037 | (2014.01) |

(52) U.S. Cl.
CPC ............... C09D 5/22 (2013.01); C09D 11/037 (2013.01); G01N 21/6408 (2013.01); G01N 2201/062 (2013.01)

(58) Field of Classification Search
CPC .... C09D 11/037; C09D 5/22; G01N 21/6408; G01N 2201/062
See application file for complete search history.

(56) References Cited

U.S. PATENT DOCUMENTS

| | | | |
|---|---|---|---|
| 353,666 | A | 12/1886 | Crane, Jr. |
| 2,742,631 | A | 4/1956 | Rajchman et al. |
| 3,614,430 | A | 10/1971 | Berler |
| 6,576,155 | B1 | 6/2003 | Barbera-Guillem |
| 6,692,031 | B2 | 2/2004 | McGrew |
| 2008/0277626 | A1 | 11/2008 | Yang et al. |
| 2009/0045360 | A1 | 2/2009 | Wosnick et al. |

OTHER PUBLICATIONS

Allison, S. et al.; "Nanoscale thermometry via the fluorescence of YAG:Ce phosphor particles: Measurements from 7 to 77 degrees C"; Nanotechnology 14 (2003); pp. 859-863.
Chen, Chieh-Wei et al.; "Evaluations of the Chemical Stability and Cytotoxicity of CuInS2 and CuInS2/ZnS Core/Shell Quantum Dots"; J. Phys. Chem. 2015; 119; pp. 2852-2860.
Li, Liang et al.; "Efficient Synthesis of Highly Luminescent Copper Indium Sulfide-Based Core/Shell Nanocrystals with Surprisingly Long-Lived Emission"; J. Am. Chem. Soc. 2011; 133; pp. 1176-1179.
McDaniel, Hunter et al.; "An integrated approach to realizing high-performance liquid-junction quantum dot sensitized solar cells"; Nature Communications, Dec. 10, 2013; 10 pages.
McDaniel, Hunter et al.; "Simple yet Versatile Synthesis of CuInSe$_x$S$_{2-x}$ Quantum Dots for Sunlight Harvesting"; J. Phys. Chem. 2014; 118; pp. 16987-16994.
Olesiak, J. and Weller, H.; "Synthesis and Application of Colloidal CuInS2 Semiconductor Nanocrystals"; ACS Appl. Mater. Interfaces 2013; 5; pp. 12221-12237.
He, Y. et al.; "Exploring Mn-Doped ZnS Quantum Dots for the Room-Temperature Phosphorescence Detection of Enoxacin in Biological Fluids"; Analytical Chemistry; vol. 80, No. 10; May 15, 2008; 7 pages.

(Continued)

*Primary Examiner* — Mark R Gaworecki
(74) *Attorney, Agent, or Firm* — John A. Fortkort; Fortkort & Houston PC

(57) ABSTRACT

A security ink is provided which includes a liquid medium having a plurality of quantum dots disposed therein. Upon excitation with a suitable light source, the ink exhibits a quantum yield greater than 30%, and a photoluminescence which has a lifetime of more than 40 nanoseconds and which varies by at least 5% across the emission spectrum of the quantum dots. Also disclosed are apparatuses for using the same for anti-counterfeit or authentication purposes, which uniquely identifying the presence of photoluminescent materials by spectrally resolving their photoluminescence lifetime.

21 Claims, 9 Drawing Sheets

(56) References Cited

OTHER PUBLICATIONS

Panthani, M. et al.; "In Vivo Whole Animal Fluorescence Imaging of a Microparticle-Based Oral Vaccine Containing (CuInSe x S2-x)/ZnS Core/Shell Quantum Dots"; Nano Letters 2013, 13; pp. 4294-4298.

Pons, T. et al.; "Cadmium-Free CuInS2/ZnS Quantum Dots for Sentinel Lymph Node Imaging with Reduced Toxicity"; ACSNano; vol. 4, No. 5; 2010; pp. 2531-2538.

Stolle, C. et al.; "Nanocrystal photovoltaics: a review of recent progress"; Current Opinion in Chemical Engineering; 2013; 2; pp. 160-167.

Tan, Z. et al.; "Near-Band-Edge Electroluminescence from Heavy-Metal-Free Colloidal Quantum Dots"; Advanced Materials; 2011; 23; pp. 3553-3558.

Trizio, L. et al.; "Strongly Fluorescent Quaternary Cu—In—Zn—S Nanocrystals Prepared from CuI-xInS2 Nanocrystals by Partial Cation Exchange"; J. Chem. Mater. 2012; 24; pp. 2400-2406.

Zhang, W. et al.; "Color-Tunable Highly Bright Photoluminescence of Cadmium-Free Cu-Doped Zn—In—S Nanocrystals and Electroluminescence"; J. Chem. Mater. 2014; 26; pp. 1204-1212.

Zhong, H. et al.; "Tuning the Luminescence Properties of Colloidal I-III-VI Semiconductor Nanocrystals for Optoelectronics and Biotechnology Applications"; J. Phys. Chem. Lett. 2012; 3; pp. 3167-3175.

QUANTUM DOT SECURITY INKS

FIELD OF THE DISCLOSURE

The present disclosure relates generally to photoluminescent materials, and more specifically to security ink compositions containing photoluminescent materials such as quantum dots, and to apparatuses for using the same for anti-counterfeit or authentication purposes.

BACKGROUND OF THE DISCLOSURE

Watermarks have been integrated into documents to verify authenticity since at least as early as the 1200's. The concept was to apply a unique, hard-to-replicate design feature that could quickly be identified by a stakeholder. This type of approach was applied in U.S. 353,666 (Crane, Jr.), entitled "Watermarked Paper" and filed in 1886, which notes that "when the paper thus produced is examined against the light", unique features can be observed.

Photoluminescence (PL) is the emission of light (electromagnetic radiation, photons) after the absorption of light. It is one form of luminescence (light emission) and is initiated by photoexcitation (excitation by photons). Following photon excitation, various charge relaxation processes can occur in which other photons with a lower energy are re-radiated on some time scale. The energy difference between the absorbed photons and the emitted photons, also known as Stokes shift, can vary widely across materials from nearly zero to 1 eV or more. Time periods between absorption and emission may also vary, and may range from the short femtosecond-regime (for emissions involving free-carrier plasma in inorganic semiconductors) up to milliseconds (for phosphorescent processes in molecular systems). Under special circumstances, delay of emission may even span to minutes or hours. Further, for a given material or mixture of materials, the emission lifetime can depend on the excitation and emission wavelength.

Some uses of luminescent security inks for authentication are known to the art. This may be appreciated, for example, with respect to U.S. Pat. No. 2,742,631 (Rajchman et al.), entitled "Methods For Recording And Transmitting Information Using Phosphors", which was filed in 1954, and U.S. Pat. No. 3,614,430 (Berler), entitled "Fluorescent-Ink-Inprinted Coded Document And Method And Apparatus For Use In Connection Therewith", which was filed in 1969.

SUMMARY OF THE DISCLOSURE

Figure 1:
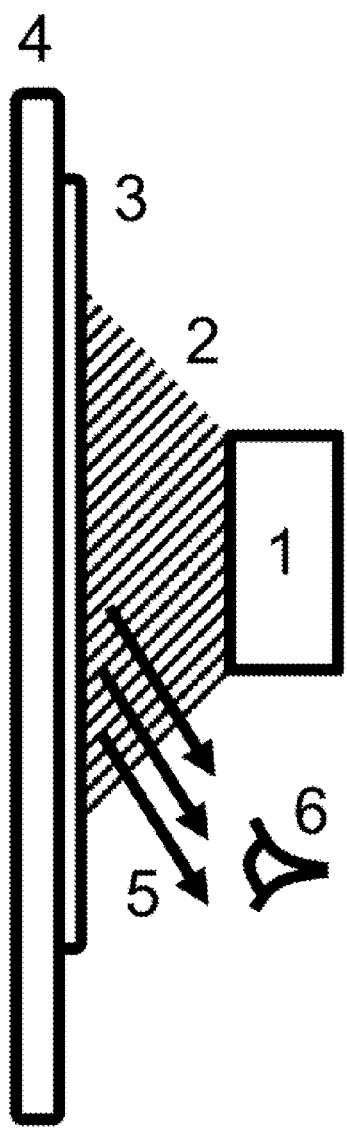
FIG. 1 is a schematic illustration of a typical overt authentication system, wherein an observer excites the security ink with a light source and visually observes the resulting visible fluorescence.

In one aspect, a security ink is provided which comprises (a) a liquid medium; and (b) a plurality of quantum dots disposed in said medium which, upon excitation with a light source, exhibit a quantum yield greater than 30%, and a photoluminescence which has at least one lifetime of more than 40 nanoseconds but less than 1 millisecond and which varies by at least 5% across the emission spectrum of the quantum dots.

In another aspect, and in combination with a security ink, an optical apparatus for analyzing said security ink is provided. The optical apparatus comprises (a) a time-varying light source which excites said security ink, thereby causing said security ink to emit an emission spectrum having first and second distinct regions which are characterized by first and second distinct lifetimes; (b) at least one photodetector; (c) a first optical element which allows only said first region of said emission spectrum from an optical signal to pass through it; (d) a second optical element which allows only said second region of said emission spectrum from an optical signal to pass through it; and (e) an electronics module which determines the photoluminescence lifetime of said security ink over said first and second regions by monitoring at least one time or frequency response of said at least one photodetector.

In a further aspect, a method is provided for verifying the authenticity of an article which bears a security mark. The method comprises (a) irradiating the security mark with a time-varying light source; (b) ascertaining at least one portion of the emissions spectrum of the irradiated security mark with at least one photodetector; (c) determining the photoluminescence lifetime of said security mark by monitoring the time or frequency response of said photodetector; and (d) verifying the authenticity of the article only if the security mark exhibits a photoluminescence which has a lifetime that falls within the range of appropriate values for each portion of the photoluminescence spectrum for which the photoluminescence lifetime of said security mark was ascertained.

In still another aspect, method for authenticating an article as belonging to a set of authentic articles, wherein each member of the set of authentic articles bears an inked security mark that emits a photoluminescence spectrum in response to being excited by a time-varying light source that emits pulses of light at a plurality of frequencies, and wherein the emitted photoluminescence spectrum is characterized by a range of lifetimes. The method comprises (a) determining whether the article to be authenticated contains a security mark; (b) if the article contains a security mark, irradiating the security mark with an instance of said time-varying light source, and determining the upper and lower bounds for the lifetime of at least one portion of said photoluminescence spectrum emitted by the irradiated security mark; and (c) authenticating the article only if (i) the article contains a security mark, and (ii) the irradiated security mark emits a photoluminescence having a lifetime that falls within predetermined upper and lower bounds characteristic of an authentic article for each portion of the photoluminescence spectrum for which the photoluminescence lifetime of said security mark was ascertained.

In yet another aspect, a method is provided for authenticating an article as belonging to a set of authentic articles, wherein each member of the set of authentic articles bears an inked security mark that emits a photoluminescence spectrum in response to being excited by a time-varying light source, and wherein the emitted photoluminescence spectrum is characterized by a range of lifetimes. The method comprises (a) determining whether the article to be authenticated contains a security mark; (b) if the article contains a security mark, (i) irradiating the security mark with a time-varying light source, wherein said time-varying light is created with a first electrical signal, and (ii) capturing a portion of the emission spectrum of the irradiated article with at least one photodetector; (c) determining the phase differences between the first electrical signal and a second electrical signal of the same frequency which is received from said photodetector in response to the captured portion of the emission spectrum; (d) determining the lifetimes of the photoluminescence of the irradiated security mark from the determined phase differences; and (e) authenticating the article only if (i) the article contains a security mark, and (ii) the irradiated security mark emits a photoluminescence spectrum whose determined lifetimes fall within the range of lifetimes characteristic of an authentic article.

DETAILED DESCRIPTION

1. Background

Colloidal semiconductor nanocrystals, commonly known as quantum dots (QDs), provide various size-tunable optical properties, including PL, and may be inexpensively processed from liquids. In particular, they are very effective at absorbing a broad spectrum of light and then converting that energy into emitted light of a single color that is determined by their size. Optical properties (such as, for example, absorption and emission spectra, PL lifetimes and Stokes shift) can be programmed into these materials by tailoring the manufacturing conditions to realize different sizes, shapes, compositions, and/or heterostructuring. This fundamental property of QDs has spurred research and development of fluorescence biolabeling, color-specific light-emitting-diodes, and vibrant displays. However, the current generation of QDs are toxic and far too expensive to reach most markets. There is thus a unique opportunity for QDs that are both low-cost and non-toxic as active elements of luminescent composites for security inks (e.g., overt and covert optical features) and other applications (e.g., lighting, solar, safety, design).

It became clear in the late 1990's that the emerging technology of QDs might be particularly well suited as fluorophores for security inks One of the earliest reports of QD security inks may be found in U.S. Pat. No. 6,576,155 (Barbara-Guillem), entitled "Fluorescent Ink Compositions Comprising Functionalized Fluorescent Nanocrystals", which was filed in 1998. This reference notes that a "mark is invisible to the unaided eye, but that can be detected as fluorescence upon excitation with an activating light of a suitable excitation wavelength spectrum."

The concept of using the fluorescence lifetime of quantum dots may be found in U.S. Pat. No. 6,692,031 (McGrew), entitled "Quantum Dot Security Device And Method", which was filed on Sep. 18, 2001. McGrew saw QDs as being advantageous over dyes (alternative fluorophore) because dyes typically have a very fast PL lifetime, on the order of a few nanoseconds. However, McGrew incorrectly claimed that the lifetime of typical CdSe QDs was "hundreds of nanoseconds", which is only the case if the QDs are very poorly passivated such that the emission arises from surface states. In that case, the PL QY of the dots is very low, typically <1%, with the result that the emission is far too weak to be of practical use. However, in well passivated CdSe-based QDs that have high QY (>50%), the emission lifetime is much faster, on the order of 15-30 ns at room temperature (see, e.g., Li, L. A.; Pandey, A.; Werder, D. J.; Khanal, B. P.; Pietryga, J. M.; Klimov, V. I. *J. Am. Chem. Soc.* 2011, 133, 1176). Similarly, typical high-efficiency inorganic phosphors such as yttrium aluminum garnet (YAG) have PL lifetimes on the order of 20 ns (see, e.g., Allison, S. W.; Gillies, G. T.; Rondinone, A. J.; Cates, M. R. *Nanotechnology* 2013, 14, 859).

In more recent references such as U.S. 2009/0045360 (Wosnick), entitled "Quantum Dot-Based Luminescent Marking Material", and U.S. 2008/0277626 (Yang), entitled "Quantum Dot Fluorescent Inks", the focus has been on the spectral signatures of a QD based security ink. For example, Wosnick teaches "materials comprising two or more luminescent marking materials, wherein each luminescent marking material, when exposed to activating radiation, has a unique narrow emission band". Yang teaches materials with a wider range of emissions between "about 450 nm and 2500 nm". Yang also teaches I-III-VI semiconductors such as $CuInGaS_2$, $CuInGaSe_2$, $AgInS_2$, $AgInSe_2$, and $AgGaTe_2$ as examples of materials that the "quantum dot core can comprise".

Nanocrystal quantum dots of the I-III-VI class of semiconductors, such as $CuInS_2$, are of growing interest for applications in optoelectronic devices such as solar photovoltaics (see, e.g., PVs, Stolle, C. J.; Harvey, T. B.; Korgel, B. A. Curr. Opin. Chem. Eng. 2013, 2, 160) and light-emitting diodes (see, e.g., Tan, Z.; Zhang, Y.; Xie, C.; Su, H.; Liu, J.; Zhang, C.; Dellas, N.; Mohney, S. E.; Wang, Y.; Wang, J.; Xu, J. Advanced Materials 2011, 23, 3553). These quantum dots exhibit strong optical absorption and stable efficient photoluminescence that can be tuned from the visible to the near-infrared (see, e.g., Zhong, H.; Bai, Z.; Zou, B. J. Phys. Chem. Lett. 2012, 3, 3167) through composition and quantum size effects. In fact, Grätzel cells sensitized by specifically engineered I—III-VI quantum dots have recently been shown to offer excellent stability and certified power conversion efficiencies of >5%. (see McDaniel, H.; Fuke, N.; Makarov, N. S.; Pietryga, J. M.; Klimov, V. I. Nat. Commun. 2013, 4, 2887). Alloyed CuInZnSeS QDs are particularly attractive for luminescent security inks because of their low toxicity, long term stability, nearly ideal PL lifetime, and other unique optical properties. In the security inks and methods of authentication disclosed in that reference, spectrally resolving the PL lifetime is surprisingly simple and cost-effective using this material.

The current generation of security inks and methods of their authentication have several major drawbacks that limit their utility. First, optical spectra alone can be easily reproduced by one or a combination of fluorophores that are widely available. Second, although one simple way to distinguish between such fluorophores could be achieved by resolving their PL lifetime, the PL lifetime of most emissive materials is less than 30 nanoseconds or longer than 100's of microseconds. Distinguishing between a PL lifetime of a few nanoseconds (or less) and tens of nanoseconds is a non-trivial undertaking with typical electronics, since it requires pulsed excitation and detection with bandwidths on the order of hundreds of 1 MHz.

For example, at present, an off the shelf LED which may be obtained from typical suppliers at a cost of a few dollars has a rise and fall time of about 10 ns, or a 20 ns pulse width (at shortest). Upgrading to a ~1 ns pulse width LED will cost about $3,000 retail, while the price of a 200 ps pulse-capable LED is about $10,000. In order to accurately measure the PL lifetime of a material, the excitation pulse width should be shorter than the PL lifetime, since otherwise the measurement will consistently produce the LED temporal behavior only. Therefore, lifetimes longer than tens of nanoseconds are needed in order to distinguish materials inexpensively, since otherwise, costly fast/frequent pulses and ultrafast detection are required.

Conversely, lifetimes which are too long—for example, manganese-doped zinc sulfide nanocrystals have a 2 ms PL lifetime (see He, Y.; Wang, H.-F.; Yan, X.-P. Anal. Chem. 2008, 80, 3832)—will take too long for authentication, since in that case, the excitation frequency must be much less than the inverse of the PL lifetime. For example, if one attempted to pulse a 2 ms fluorophore at 50 kHz, the signal would not be able to decay appreciably between pulses (1/2 ms=0.5 kHz<<50 kHz). In order to build up signal to noise, it is estimated that at least 1000 cycles must be completed. Hence, a 2 ms PL lifetime needs at least 2 seconds worth of data for each frequency, while a 500 ns PL lifetime would need only about 0.5 ms for each frequency.

Thirdly, most QD materials available today are highly hazardous. The use of cadmium-based fluorophore is a non-starter for most security ink applications, since it is a known carcinogen that bio-accumulates in the human body. The most common cadmium-free QD material, indium phosphide, is also a known carcinogen. For near-IR emission, lead-based QDs are typically utilized. There is a clear and urgent need for QD fluorophores which are non-carcinogenic and have PL lifetimes of order 100's of nanoseconds.

In addition, there are also problems with methods of authentication, in part because the security ink technology was not conceived which demanded new authentication concepts. Although McGrew teaches that PL lifetimes can be combined with spectral signatures for enhanced authentication, the reference does not teach spectrally resolving the PL lifetime. A material which contains a PL lifetime that varies over the detection spectral bandwidth would produce an average lifetime if measured over the entire spectrum. Such an average would not be a single exponential decay, but rather a multi-exponential linear sum of the contributing decays. A single exponential decay is important for low-cost authentication because it allows for simple, unambiguous determination of the lifetime. Further, typical methods for spectrally resolving a lifetime would require the pulsed emission to pass through a diffraction grating or prism in order to split the spectrum spatially for detection. Such spectral splitting requires large volumes and, in some cases, moving parts, which slows the authentication process and/or increases the size of the authenticator. Hence, in order to take advantage of the security inks disclosed herein, new methods of compact and rapid authentication are needed wherein the PL lifetime is spectrally resolved (or, equivalently, wherein the PL spectrum is temporally resolved).

2. Overview

Full spectrum (visible to near-IR, 400-1400 nm) photoluminescent non-toxic security inks are needed to create unique spectral and temporal signatures on high value items including, but not limited to banknotes, credit cards, important documents, pharmaceuticals, and luxury goods. Existing methods for rapid, compact, and low-cost authentication of these security inks have not yet been envisioned, but are required in parallel.

Novel security inks are disclosed herein which, in a preferred embodiment, contain non-carcinogenic QDs having tunable PL spectra with peaks in the visible (400-650 nm) to near-IR (650-1400 nm) and spectrally varying PL lifetimes in the optimal range of 100-1000 ns. In some embodiments, the ink may contain multiple sizes and/or compositions of QD emitters to modify the spectrum and/or temporal characteristics further. A preferred, though non-limiting, photoluminescent material for this purpose is CuInZnSeS QDs.

Methods of authentication of these security inks are also disclosed which involve pulsed LED excitation and spectrally-resolved detection. The PL decay may be characterized in the frequency domain or in the time domain by probing of the delay between detected photons and the excitation. This may be accomplished, for example, by measuring the phase relationship between the excitation waveform and the detected waveform. The spectral resolving capability may be achieved by filtering the light prior to detection with a long pass, short pass, or band pass filter. An exemplary long-pass filter material for this purpose may comprise the same or similar QDs as are used in the ink; however, the QDs in the filter material are preferably rendered non-emissive or weakly-emissive.

The compositions, systems and methodologies disclosed herein represent an improvement over previous generations of authentication technologies in which it was typical for only the spectral signatures to be observed, since temporal characterization was not economically viable. Moreover, in previous authentication methodologies, the temporal response of a security ink was not spectrally resolved. The compositions, systems and methodologies disclosed herein may be utilized to provide a simple, safe, rapid, and cost-effective solution to the counterfeiting of high value items.

3. Definitions and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly indicates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure relates. Suitable methods and compositions are described herein for the practice or testing of the compositions, systems and methodologies described herein. However, it is to be understood that other methods and materials similar or equivalent to those described herein may be used in the practice or testing of these compositions, systems and methodologies. Consequently, the compositions, materials, methods, and examples disclosed herein are illustrative only, and are not intended to be limiting. Other features of the disclosure will be apparent to those skilled in the art from the following detailed description and the appended claims.

Unless otherwise indicated, all numbers expressing quantities of components, percentages, temperatures, times, and so forth, as used in the specification or claims are to be understood as being modified by the term "about." Unless otherwise indicated, non-numerical properties such as colloidal, continuous, crystalline, and so forth as used in the specification or claims are to be understood as being modified by the term "substantially," meaning to a great extent or degree. Accordingly, unless otherwise indicated implicitly or explicitly, the numerical parameters and/or non-numerical properties set forth are approximations that may depend on the desired properties sought, the limits of detection under standard test conditions or methods, the limitations of the processing methods, and/or the nature of the parameter or property. When directly and explicitly distinguishing embodiments from discussed prior art, the embodiment numbers are not approximates unless the word "about" is recited.

Carcinogen: A material that has been shown to directly or indirectly cause cancer in any mammal.

Phase Measurement Device: A device that measures phase. Examples include, but are not limited to, lock-in amplifiers, impedance gain phase analyzers, oscilloscopes, and network analyzers.

Photoluminescence (PL): The emission of light (electromagnetic radiation, photons) after the absorption of light. It is one form of luminescence (light emission) and is initiated by photoexcitation (excitation by photons).

Polymer: A large molecule, or macromolecule, composed of many repeated subunits. Polymers range from familiar synthetic plastics such as polystyrene or poly(methyl methacrylate) (PMMA), to natural biopolymers such as DNA and proteins that are fundamental to biological structure and function. Polymers, both natural and synthetic, are created via polymerization of many small molecules, known as monomers. Exemplary polymers include poly(methyl methacrylate) (PMMA), polystyrene, silicones, epoxy resins, and nail polish.

Toxic: Denotes a material that can damage living organisms due to the presence of phosphorus or heavy metals such as cadmium, lead, or mercury.

Quantum Dot (QD): A nanoscale particle that exhibits size-dependent electronic and optical properties due to quantum confinement. The quantum dots disclosed herein preferably have at least one dimension less than about 50 nanometers. The disclosed quantum dots may be colloidal quantum dots, i.e., quantum dots that may remain in suspension when dispersed in a liquid medium. Some of the quantum dots which may be utilized in the compositions, systems and methodologies described herein are made from a binary semiconductor material having a formula MX, where M is a metal and X typically is selected from sulfur, selenium, tellurium, nitrogen, phosphorus, arsenic, antimony or mixtures thereof. Exemplary binary quantum dots which may be utilized in the compositions, systems and methodologies described herein include CdS, CdSe, CdTe, PbS, PbSe, PbTe, ZnS, ZnSe, ZnTe, InP, InAs, $Cu_2S$, and $In_2S_3$. Other quantum dots which may be utilized in the compositions, systems and methodologies described herein are ternary, quaternary, and/or alloyed quantum dots including, but not limited to, ZnSSe, ZnSeTe, ZnSTe, CdSSe, CdSeTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, $CuInS_2$, $CuInSe_2$, $CuInGaSe_2$, $CuInZnS_2$, $CuZnSnSe_2$, $CuIn(Se,S)_2$, $CuInZn(Se,S)_2$, and $AgIn(Se,S)_2$ quantum dots, although the use of non-toxic quantum dots is preferred. Embodiments of the disclosed quantum dots may be of a single material, or may comprise an inner core and an outer shell (e.g., a thin outer shell/layer formed by any suitable method, such as cation exchange). The quantum dots may further include a plurality of ligands bound to the quantum dot surface.

Security ink: A liquid solution applied by inkjet printing, stamping, scribing, spraying, or other marking methods that imparts uniquely identifiable features onto a substrate for the purposes of authentication or counterfeit prevention.

Emission spectrum: Those portions of the electromagnetic spectrum over which a mark exhibits PL (in response to excitation by a light source) whose amplitude is at least 1% of the peak PL emission.

4. Best Mode

Figure 2:
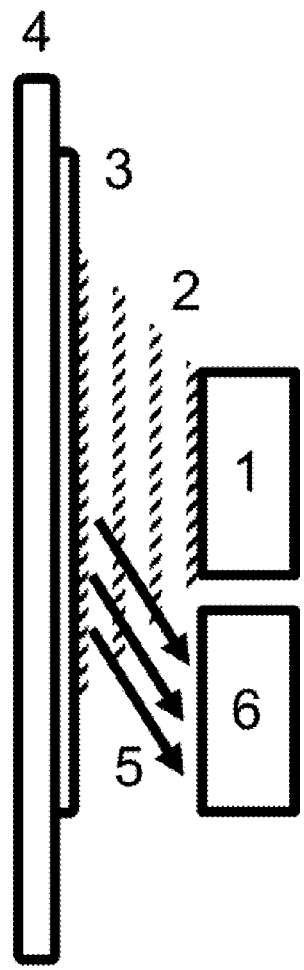
FIG. 2 is a schematic illustration of covert authentication system in which the security ink is excited with a time-varying light source (such as, for example, a blue or UV LED), and wherein the time-varying fluorescence is subsequently measured by a photodetector. In this case, the spectral resolution is achieved intrinsically by the choice of the photodetector.
Figure 3:
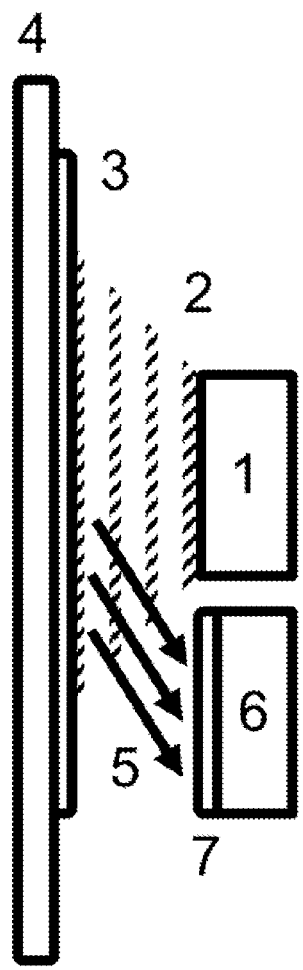
FIG. 3 is a schematic illustration of covert authentication system in which the security ink is excited with a time-varying light source (such as, for example, a blue or UV LED), and wherein the time-varying fluorescence is subsequently measured by a photodetector after passing through a spectrum selecting component. In this case, the spectral resolution is achieved by choice of the spectrum selecting component (in some embodiments, the spectrum selecting component may be a filter or film of quantum dots) and also by choice of photodetector.
Figure 4:
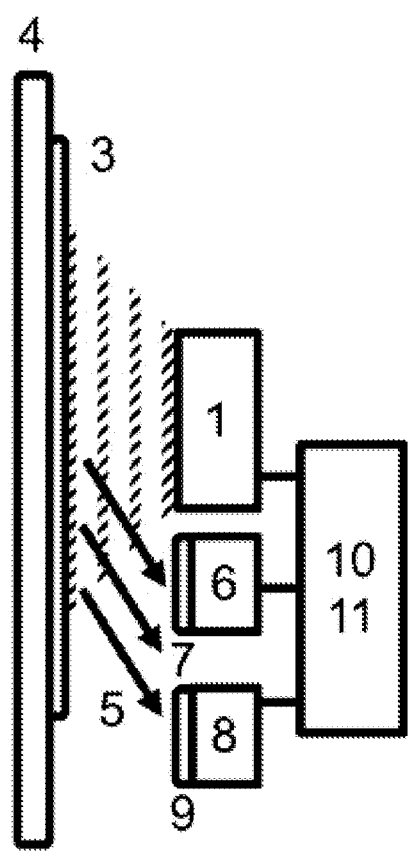
FIG. 4 is a schematic illustration of a covert authentication system in which the security ink is excited with a time-varying light source (such as, for example, a blue or UV LED), and wherein the time-varying fluorescence is subsequently measured by multiple photodetectors after passing through one or more spectrum selecting components. In this case, the spectral resolution is achieved by choice of the spectrum selecting components in front of each detector (in some embodiments, these spectrum selecting components may be different filters or films of different quantum dots), and also by the choice of the photodetectors.
Figure 5:
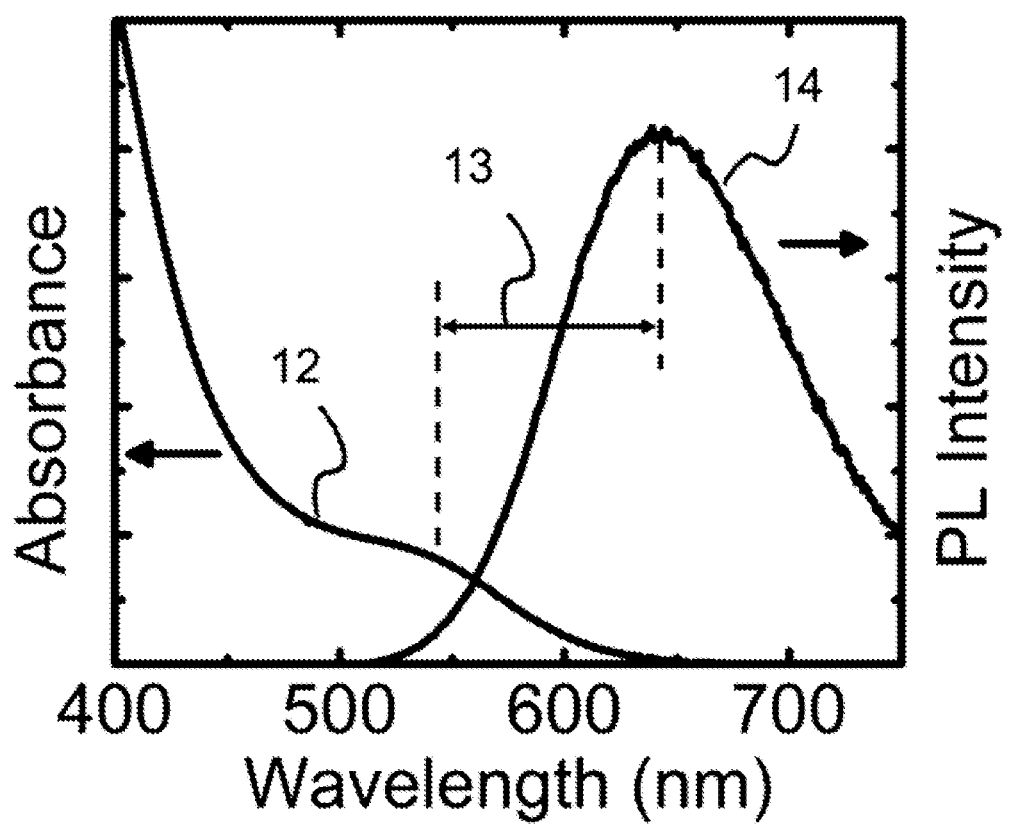
FIG. 5 is a graph of a typical absorption and photoluminescence spectra for exemplary CuInZnSeS quantum dots. These QDs are substantially free of toxic elements and are believed to be non-carcinogenic. The QDs have an emission quantum yield of >70%.

The preferred embodiment of the systems and methodologies disclosed herein includes the use of a security ink comprising a mixture of one or more sizes and/or compositions of CuInZnSeS QDs (see FIGS. 5-6), and the spectrally-resolved detection of the temporal signatures (see FIG. 7) of the security ink with one or more photodetectors (see FIGS. 2-4). FIG. 4 depicts the mode with the strongest authentication, wherein light source 1 (which may be, for example, a blue or UV LED) emits a time-varying excitation 2 upon a security ink containing QDs 3 applied to a substrate 4. Then, the time-varying photoluminescence from the ink 5 is measured by first and second photodetectors 6 and 8 after being spectrally resolved using first and second optical elements 7 and 9 which may be, for example, optical filters. In some embodiments, the first and second optical elements 7 and 9 may comprise thin films containing non-emissive versions of the same or similar QDs in the security ink.

For example, in some embodiments of the device of FIG. 4, the time-varying light source 1 may excite the security ink 3, thereby causing the security ink to emit an emission spectrum having first and second distinct regions which are characterized by first and second distinct lifetimes. The first optical element 7 may be disposed in a first optical path which includes the first photodetector 6, and the second optical element 9 may be disposed in a second optical path which includes the second photodetector 8. In such a configuration, the first optical element 7 may act to allow only the first region of the emission spectrum from an optical signal to pass through it, and the second optical element 9 may act to allow only the second region of the emission spectrum from an optical signal to pass through it. A microcontroller 11 typically in electrical communication with the first 6 and second 8 photodetectors that may then determine the photoluminescence lifetime of the security ink 3 over the first and second regions by monitoring the time or frequency response of the first 6 and second 8 photodetectors. Additionally, a phase measuring device 10 may determine a phase relationship between the electrical signal producing time-varying light 2 and the electrical response of the first 6 and second 8 photodetectors, and then provide that phase information to the microcontroller 10 for determination of the first and second distinct lifetimes.

Figure 6:
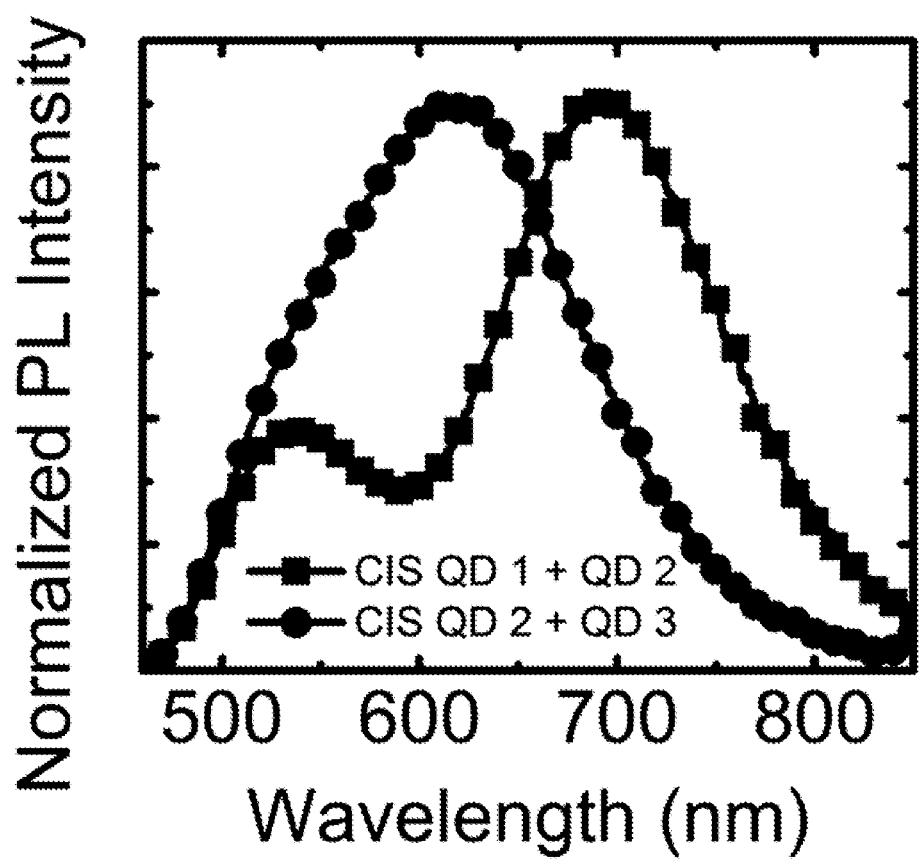
FIG. 6 is a graph of the photoluminescence arising from two different mixtures of CuInZnSeS quantum dots inks on a paper substrate. The shape of the spectrum, including the number of peaks, number of troughs, slope of the spectrum, and other signatures, is tailored based on the size and composition of the quantum dots chosen. The QDs mixtures have an emission quantum yield of >50%.
Figure 7:
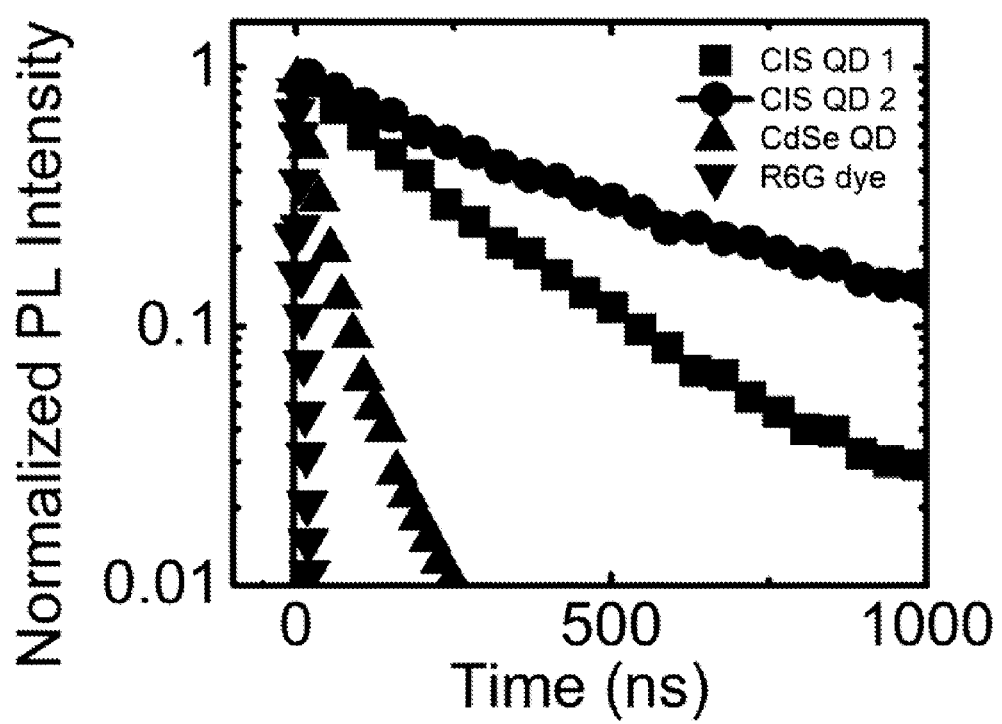
FIG. 7 is a graph of the photoluminescence decay arising from two different photoluminescent materials that may be used in security inks The PL decay from different CuInZnSeS QDs having single exponential decays of 417 ns (CIS QD 1, squares) and 209 ns (CIS QD 2, circles) is compared with typical CdSe QDs having a 30 ns lifetime (up triangles) and rhodamine 6G dye having a 5 ns lifetime (down triangles).

Additional spectral resolution may be achieved by choice of the photodetectors. For example, a typical low-cost photodetector is a silicon photodiode which has an absorption onset of about 1100 nm. When such a photodetector is combined with the QDs having the absorption spectrum 12 shown in FIG. 5, which allow only light with wavelengths longer than 600 nm, the resulting combination selects only emission in the range of 600 to 1100 nm. Such a set-up would allow for detection of the photoluminescence 14 shown in FIG. 5, enabled by the large separation 13 between the absorption and emission of CuInZnSeS QDs. Typical QDs would significantly self-absorb their own PL, preventing its detection. Choosing a different filter and/or a different photodetector will adjust the spectral resolution of the detection so that specific bands of the photoluminescence (such as that shown in FIG. 6) can be selected for temporal characterization. FIG. 7 shows the PL decay from a mixture of different CuInZnSeS QDs, where the PL from each type of QD is selected by a monochromator (circles and squares) having single exponential decays of 209 ns (observed near 700 nm) and 417 ns (observed near 550 nm).

5. Making and Using the Best Mode

In the best mode of the system depicted in FIG. 4, QDs may be added to an existing ink that will typically result in a polymer matrix being formed for an added pigment such as QDs. The ink containing the QDs may then be applied to a substrate by any suitable method of ink deposition including, but not limited to, inkjet printing, stamping, scribing, spraying, or other suitable marking methods as are known to the art. The detector utilized in this methodology is preferably a compact and handheld device which preferably includes a pulsed LED, color-selective filters, photodetectors, at least one microcontroller, and other necessary electronics (such as, for example, a lock-in amplifier). Such devices are commercially available, and may be manufactured using techniques that are well known in the consumer electronics industry.

For the overt mode shown in FIG. 1 (described below), the security ink is illuminated by a handheld light source (such as, for example, a blue or UV LED flashlight), and the resulting visible photoluminescence is observed visually for a simple, low-tech, first authentication, as desired. Counterfeiters may erroneously believe that the overt mode shown in FIG. 1 is, in fact, the only security feature, and may thus fail to ensure that the covert modes shown in FIGS. 2-4 are adequately imparted.

The compositions, systems and methodologies disclosed herein are especially suitable for validating the authenticity of high value items. Such validation may occur in the time-domain or the frequency domain.

In the time domain version of the system depicted in FIG. 4, the light source 1 is triggered to emit pulses of light 2 at multiple different frequencies. Thus, in the time domain, the resulting excitation (light source) signals are manifested as short-duration step functions.

The frequencies of excitation should be of the order of the inverse of the PL lifetimes of the security ink to be characterized. For example, at a very low frequency compared with the inverse of the PL lifetime, the average amount of light reaching the detectors will depend linearly on the amplitude and the frequency of the excitation, since the ink can fully relax between pulses. At a very high frequency compared with the inverse of the PL lifetime, the average amount of light reaching the detectors will depend on the amplitude of the excitation, but will not depend much (if at all) on the frequency of excitation (or the PL lifetime) because the PL of the ink will only slightly decay before the next pulse comes to re-excite the ink. Therefore, if two or more frequencies are chosen to excite the ink in the range of the inverse of the lifetimes to be measured, upper and lower bounds may be placed on the PL lifetime of the ink, thereby validating the covert feature. Using spectral selection of the PL of the ink adds additional PL lifetime bounds for different bands of the emission spectrum, thereby strengthening the security.

The time-domain approach is simple in that only the average power from the photodetectors must be observed, thus simplifying the electronics. However, multiple frequencies of excitation must be used, which could lengthen the time needed for confident authentication.

In the frequency domain version of the system depicted in FIG. 4, the light source 1 is triggered to emit sinusoidal light 2 at a single frequency or at multiple frequencies. Consequently, in the frequency domain, the signals are manifested as delta functions at the given frequencies. It is preferred that the frequency of excitation is on the order of the inverse of the PL lifetimes of the security ink to be characterized.

The electrical impulse creating the excited light is sent to a lock-in amplifier or other phase analyzer that compares it to the electrical impulse(s) coming from the photodetector(s) at the same frequency. The lock-in amplifier or other phase analyzer then determines the phase relationship between the signals and the phase differences are related to the lifetimes of the PL detected (unknown) and the frequency of the excitation (known). Hence, by using the phase difference between the excitation and PL emission from the ink, the lifetime of the ink may be determined. Using spectral selection of the PL of the ink adds PL lifetime information for different bands of the emission spectrum, thereby strengthening the security.

The frequency-domain approach is more complicated than the time-domain approach because it requires lock-in detection or other phase analysis hardware. However, fewer (or even one) frequencies of excitation may be used in this approach, which will typically shorten the time needed for confident authentication.

Figure 8:
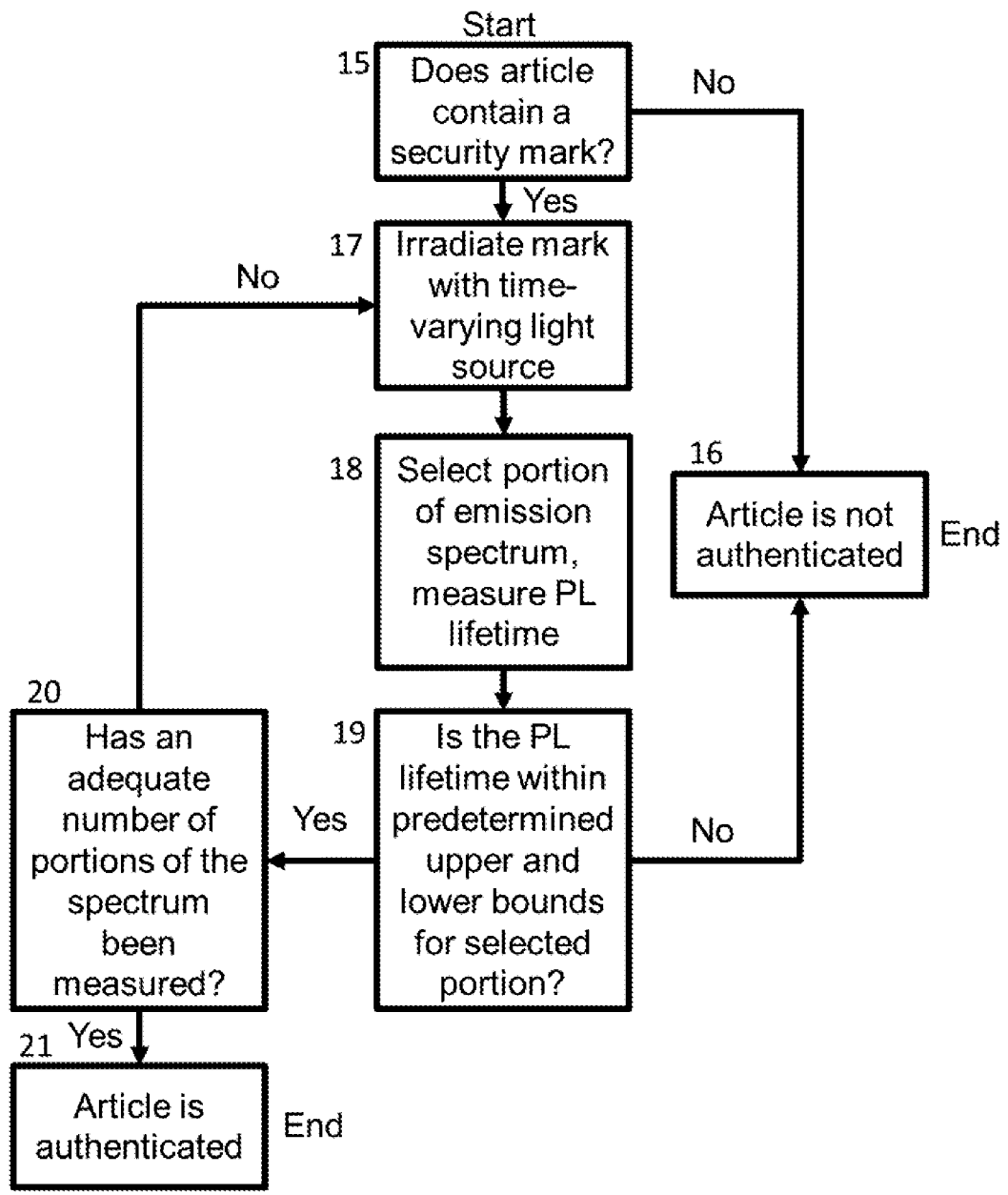
FIG. 8 is a flowchart illustrating a first embodiment of the methodology disclosed herein, and in which one or more lifetimes may be measured for an emission spectrum.

FIG. 8 illustrates a particular, non-limiting embodiment of a process in accordance with the teachings herein in which PLs are determined for one or more portions of an emissions spectrum. As seen therein, the process begins with determining whether an article to be authenticated contains a security mark 15. If not, the article is not authenticated 16, and the process ends.

If the article does contain a security mark, then the security mark is irradiated with a time-varying light source 17. A portion of the resulting emission spectrum is then selected, and the photoluminescence lifetime (PL) is measured 18. A determination is then made as to whether the measured PL is within predetermined upper and lower bounds for the selected portion of the emissions spectrum 19. If not, the article is not authenticated 16, and the process ends. If so, a determination is made as to whether the PL has been measured over an adequate number of portions of the emissions spectrum 20. If not, the process is passed to step 17. If so, the article is authenticated 21, and the process ends.

Figure 9:
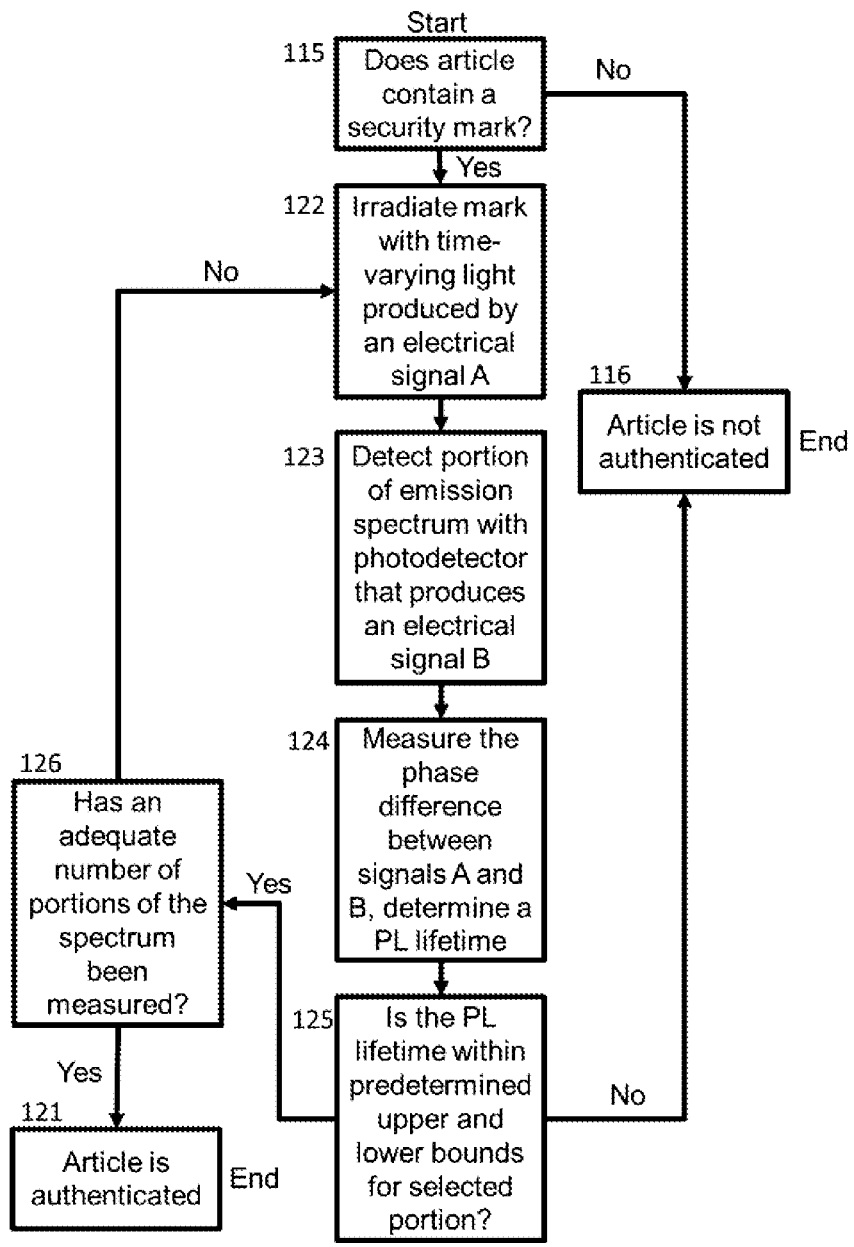
FIG. 9 is a flowchart illustrating a second embodiment of the methodology disclosed herein, and in which one or more lifetimes may be measured for an emission spectrum by measuring the phase difference between a signal A which is used to produce the time-varying light used to irradiate a mark, and a signal B produced by a photodetector used to detect emissions from the irradiated mark.

FIG. 9 illustrates another particular, non-limiting embodiment of a process in accordance with the teachings herein in which PLs are determined for one or more portions of an emissions spectrum by measuring the phase difference between a first signal used to generate the light used to irradiate an article, and a second signal produced by a photodetector that detects emissions from the irradiated article.

As seen therein, the process begins with determining whether an article to be authenticated contains a security mark 115. If not, the article is not authenticated 116, and the process ends. If the article does contain a security mark, then the security mark is irradiated with a time-varying light source 122 produced by an electrical signal A. A portion of the emission spectrum is then detected 123 with a photodetector that produces an electrical signal B. The PL lifetime is then determined 124 by measuring the phase difference between signals A and B.

A determination is then made as to whether the PL lifetime is within the predetermined upper and lower bounds for the selected portion of the emission spectrum 125. If not, the article is not authenticated 116, and the process ends. If so, a determination is made as to whether the PL has been measured over an adequate number of portions of the emissions spectrum 126. If not, the process is passed to step 122. If so, the article is authenticated 121, and the process ends.

6. Examples

The following examples are non-limiting, and are merely intended to further illustrate the compositions, systems and methodologies disclosed herein.

Example 1

This example illustrates the use of overt authentication as both a quick authentication method and a "red herring", that is, a feature intended to fool or frustrate counterfeiters.

The device utilized in this example is depicted schematically in FIG. 1. As seen therein, the device comprises a light source 1 (which may be, for example, a blue or UV LED flashlight) emitting an excitation 2 upon a security ink containing QDs 3 applied to a substrate 4. The photoluminescence 5 from the ink in the irradiated substrate 4 is then observed and spectrally resolved by an observer's eye 6. This mode exemplifies the way that photo luminescent security inks are typically authenticated, and is still an available mode for the systems and methodologies disclosed herein. More importantly, a counterfeiter seeking to circumvent the security may believe that this mode is the only mode of authentication, and hence this mode may serve as a "red herring" to frustrate the efforts of counterfeiters. It is possible to create an ink with different materials such as dyes or other types of QDs that will appear by eye the same using this overt feature, but under the other modes will not be authenticated.

As a test of this mode, CuInZnSeS QDs were dissolved in octane at 50 mg/mL and deposited onto a paper substrate. Under blue and UV LED flashlights, the deposited ink, which otherwise has a light yellow hue, glowed a bright orange.

Example 2

This example illustrates the use of covert authentication using a single, un-filtered photodetector.

As seen in FIG. 2, a system is provided in which a light source 1 (such as, for example, a blue or UV LED) emits a time-varying excitation 2 upon a security ink containing QDs 3 applied to a substrate 4. The time-varying photoluminescence from the irradiated ink 5 is measured by a photodetectors 6. Spectral resolution is achieved by choice of the photodetector 6.

Example 3

This example illustrates the use of covert authentication using a single, filtered photodetector.

As seen in FIG. 3, a system is provided in which a light source 1 (which may be, for example, a blue or UV LED) emits a time-varying excitation 2 upon a security ink containing QDs 3 applied to a substrate 4. The time-varying photoluminescence from the irradiated ink 5 is measured by a photodetector 6 after being spectrally resolved using a spectrum selecting component 7. In some embodiments, the spectrum selecting component may comprise a thin film containing non-emissive or weakly-emissive versions of the same or similar QDs in the security ink. Additional spectral resolution is achieved by choice of the photodetectors.

As a test of this mode, a mixture of two different CuInZnSeS QDs were dissolved in octane at 50 mg/mL and deposited onto a paper substrate. The resulting spectrum is shown in FIG. 6 (CIS QD 1 and CIS QD 2, squares). Under 445 nm excitation (blue), the PL decay was measured in the range of from 540 to 560 nm, selecting only the emission from CIS QD 2. The PL decay was measured using time-resolved single photon counting (Horiba FluoroMax 4 system) and single exponential decay of 417 ns was observed (see FIG. 7, circles).

7. Additional Comments

Various modifications, substitutions, combinations, and ranges of parameters may be made or utilized in the compositions, devices and methodologies described herein.

For example, in some embodiments, the photoluminescence of the security ink to be characterized by light emission may have wavelengths in the range of 400 nm to 1400 nm, more preferably in the range of 500 nm to 1300 nm, and most preferably in the range of 550 nm to 1200 nm.

In some embodiments, the photoluminescence of the security ink may be characterized by a lifetime of more than 100 ns, more than 150 ns, more than 200 ns, or more than 300 ns. Preferably, however, the photoluminescence of the security ink is less than 1 ms.

In some embodiments, the photoluminescence of the security ink may be characterized by a lifetime that varies by at least 50 ns, by at least 70 seconds, or by at least 100 ns across the emission spectrum.

In some embodiments, the photoluminescence of the security ink may be characterized by a quantum yield of at least 30%, at least 50%, at least 70%, or at least 80%.

Various light sources may be utilized in the devices and methodologies described herein to excite the security ink and/or authenticate an article bearing the ink. Preferably, these light sources are LED light sources featuring one or more LEDs, and more preferably, these light sources are selected from the group consisting of UV LEDs, blue LEDs, green LEDs and red LEDs.

The light sources utilized in the devices and methodologies described herein may oscillate at various frequencies. Thus, for example, these light sources may oscillate at frequencies of less than 40 MHz, less than 30 MHz, less than 10 MHz, or less than 5 MHz.

Various photodetectors may be utilized in the devices and methodologies described herein to analyze emissions received from an article exposed to radiation for the purposes of authentication. Thus, for example, the photodetector may selectively absorb light with wavelengths shorter than (acting as a short pass filter) 1200 nm, shorter than 1100 nm, shorter than 1000 nm, shorter than 900 nm, shorter than 800 nm, shorter than 700 nm, or shorter than 600 nm.

Various optical elements may be utilized in the optical paths of the devices and methodologies described herein. For example, in some embodiments, a spectrum selecting optical element may be placed in the optical path between the irradiated article and the photodetector, and through which the photoluminescence passes before reaching the photodetector. Such an optical element may include, for example, one or more elements selected from the group consisting of light filters, quantum dot films and colored glasses. A spectrum selecting optical element of this type may allow only a given portion of the spectrum to pass through from an optical signal incident on the spectrum selecting optical element. By way of example, some embodiments may feature a first spectrum selecting optical element disposed in a first optical path between the irradiated article and a first photodetector, and a second spectrum selecting optical element disposed in a second optical path between the irradiated article and a second photodetector. Such an arrangement allows a microcontroller to determine the lifetime of photoluminescence over two distinct optical regions of the emission spectrum. Of course, it will be appreciated that a similar approach may be utilized to determine the lifetimes of photoluminescence over any desired number of distinct optical regions of the emission spectrum.

In some embodiments, two or more distinct types of quantum dots may be utilized in the systems, methodologies and compositions described herein. These quantum dots may be compositionally distinct. For example, the security inks described herein may comprise a first type of quantum dot based on a first chemistry, and a second type of quantum dot based on a second chemistry which is distinct from the first chemistry. Thus, for example, the first type of quantum dot may comprise, for example, $CuInS_2$, while the second type of quantum dot may comprise $AgInSe_2$. Similarly, the security inks described herein may comprise a first type of quantum dot based on a first set of dimensions (or distribution of dimensions) of the quantum dots, and a second type of quantum dot based on a second set of dimensions (or distribution of dimensions) of the quantum dots which is distinct from the first set of dimensions (or distribution of dimensions) of the quantum dots. Thus, for example, the first type of quantum dot may comprise generally spherical quantum dots having a first diameter (e.g., 10 nm), and the second type of quantum dot may comprise generally spherical quantum dots having a second diameter (e.g., 30 nm).

Various phase analyzers may be utilized in the systems and methodologies described herein. These devices may include, but are not limited to, lock-in amplifiers, impedance gain phase analyzers, oscilloscopes, and network analyzers. Typically, such devices operate by measuring a phase relationship between a time-varying excitation and a time-varying photoluminescence for a security ink of the type disclosed herein.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

Moreover, it is specifically contemplated that the features described in the appended claims may be arranged in different combinations or sub-combinations without departing from the scope of the present disclosure. For example, it is contemplated that features set forth in two or more claims may be combined into a single claim without departing from the scope of the present disclosure, whether or not the resulting combination of features is explicitly disclosed elsewhere in the appended claims or disclosure.

What is claimed is:

1. A security ink, comprising:
a liquid medium; and
a plurality of quantum dots disposed in said medium which, upon excitation with a light source, exhibit a quantum yield greater than 30%, and a photoluminescence which has at least one lifetime of more than 40 nanoseconds but less than 1 millisecond and which varies by at least 5% across the emission spectrum of the quantum dots.

2. The security ink of claim 1, further comprising quantum dots composed of semiconductors that do not contain phosphorus, lead, cadmium, or mercury.

3. The security ink of claim 1, wherein said plurality of quantum dots comprises a first set of quantum dots having a first chemical composition and size, and a second set of quantum dots having a second chemical composition and size which are distinct from said first chemical composition and size.

4. The security ink of claim 1, wherein said plurality of quantum dots comprise a material selected from the group consisting of $CuInS_2$, $CuInSe_2$, $AgInS_2$, $AgInSe_2$, ZnS and ZnSe.

5. The security ink of claim 1, wherein said photoluminescence is characterized by light emission having wavelengths in the range of 450 nm to 1250 nm.

6. The security ink of claim 1, wherein said photoluminescence is characterized by a lifetime of more than 100 nanoseconds but less than 1 microsecond.

7. The security ink of claim 1, wherein said photoluminescence is characterized by a lifetime that varies by at least 10% across said emission spectrum.

8. The security ink of claim 1, wherein said photoluminescence is characterized by a lifetime that varies by at least 50 ns across said emission spectrum.

9. The security ink of claim 1, wherein said photoluminescence is characterized by a quantum yield that is greater than 50%.

10. The security ink of claim 1, wherein said photoluminescence is characterized by a quantum yield that is greater than 70%.

11. In combination with the security ink of claim 1, an optical apparatus for analyzing said security ink, comprising:
a time-varying light source which excites said security ink, thereby causing said security ink to emit an emission spectrum having first and second distinct regions which are characterized by first and second distinct lifetimes;
at least one photodetector;

a first optical element which allows only said first region of said emission spectrum from an optical signal to pass through it;

a second optical element which allows only said second region of said emission spectrum from an optical signal to pass through it; and an electronics module which determines the photoluminescence lifetime of said security ink over said first and second regions by monitoring at least one time or frequency response of said at least one photodetector.

12. The combination of claim 11, wherein said light source is selected from the group consisting of UV LEDs, blue LEDs, green LEDs and red LEDs.

13. The combination of claim 11, wherein said at least one photodetector includes first and second photodetectors, wherein said first optical element is disposed in a first optical path which includes said first photodetector, and wherein said second optical element is disposed in a second optical path which includes said second photodetector.

14. The combination of claim 11, wherein said light source oscillates with a frequency of less than 100 MHz.

15. The combination of claim 11, wherein said light source oscillates with a frequency of less than 10 MHz.

16. The combination of claim 11, wherein said first plurality of quantum dots comprise a material selected from the group consisting of $CuInS_2$, $CuInSe_2$, $AgInSe_2$, $AgInSe_2$, ZnSe and ZnS.

17. The combination of claim 11, wherein said photodetector comprises a material selected from the group consisting of silicon, germanium, cadmium sulfide, indium phosphide, copper indium diselenide, indium gallium arsenide and gallium arsenide.

18. The combination of claim 11, wherein said first and second optical components are selected from the group consisting of light filters, quantum dot films and colored glasses.

19. The combination of claim 11, wherein the security ink contains a first of quantum dots, and further comprising at least one film containing a second plurality of quantum dots through which said photoluminescence passes through before reaching said at least one photodetector, wherein said second plurality of quantum dots comprise a material selected from the group consisting of $CuInS_2$, $CuInSe_2$, $AgInSe_2$, $AgInSe_2$, ZnSe and ZnS.

20. The combination of claim 11, further comprising a microcontroller in communication with said light source and said photodetector, wherein said microcontroller characterizes the time-varying photoluminescence from said security ink.

21. The combination of claim 11, further comprising a phase measuring device in communication with said light source and said at least one photodetector, wherein said phase measuring device measures a phase relationship between a time-varying excitation and a time-varying photoluminescence from said security ink.

* * * * *